United States Patent [19]

Lane

[11] Patent Number: 5,774,177
[45] Date of Patent: Jun. 30, 1998

[54] TEXTILE FABRIC INSPECTION SYSTEM

[75] Inventor: Jeffery Scott Lane, Moore, S.C.

[73] Assignee: Milliken Research Corporation, Spartanburg, S.C.

[21] Appl. No.: 710,003

[22] Filed: Sep. 11, 1996

[51] Int. Cl.$^6$ ....................................................... H04N 7/18
[52] U.S. Cl. ............................. 348/88; 348/128; 382/111
[58] Field of Search ...................... 348/88, 128; 382/111; 356/429, 430, 431; H04N 7/18

[56] References Cited

U.S. PATENT DOCUMENTS

| | | | |
|---|---|---|---|
| 4,581,762 | 4/1986 | Lapidus et al. | 382/263 |
| 4,817,184 | 3/1989 | Thomason et al. | 382/141 |
| 4,853,970 | 8/1989 | Ott et al. | 382/266 |
| 4,876,457 | 10/1989 | Bose | 356/445 |
| 4,974,261 | 11/1990 | Nakahara | 348/128 |
| 5,394,183 | 2/1995 | Hyslop | 348/88 |

*Primary Examiner*—Howard Britton
*Attorney, Agent, or Firm*—Terry T. Moyer; George M. Fisher

[57] ABSTRACT

A method and apparatus for inspecting textile fabric which automatically detects defects within the field of view of a video camera. A frame of video information is captured and a digital image array is generated. A mask or operator is then used to generate a gradient image from the digital image array. The gradient image is then thresholded, dilated, optionally eroded, and then subjected to a blob analysis. A special operator is utilized in order to generate a gradient image which slow grey level transitions (e.g., oil spots) are identifiable.

49 Claims, 5 Drawing Sheets

SIZE THRESHOLD
USING THRESHOLD
VALUE OF 5

TEXTILE FABRIC INSPECTION SYSTEM

BACKGROUND OF THE INVENTION

A visual inspection of textile fabrics is a time consuming and thereby expensive process. Furthermore, it is also monotonous and tedious which lends itself to inaccuracies. Some fabrics such as those for clean room wipes must be virtually free of defects. Defects, in the current context, can be either structural such as knitting or weaving defects, holes, tears, and so forth or due to contaminates such as oil, grease, dirt, and so forth. Any abnormality that is visible to the unaided human eye is classified as a defect.

The present invention solves these problems in a manner not disclosed in the known prior art.

SUMMARY OF THE INVENTION

A method and apparatus for inspecting textile fabric which automatically detects defects within the field of view of a video camera. A frame of video information is captured and a digital image array is generated. A mask or operator is then used to generate a gradient image from the digital image array. The gradient image is then thresholded, dilated, optionally eroded, and then subjected to a blob analysis. A special operator is utilized in order to generate a gradient image in which slow grey level transitions (e.g., oil spots) are identifiable.

It is an advantage of this invention to detect defects without the use of human vision.

It is another advantage of this invention to speed up the inspection of textile fabrics and the manufacturing process.

Yet another advantage of this invention is to eliminate the tedious boredom associated with visually inspecting textile fabrics.

Still another advantage of this invention is to inspect fabrics with a greater accuracy than is humanly possible.

These and other advantages will be in part apparent and in part pointed out below.

BRIEF DESCRIPTION OF THE DRAWINGS

The above as well as other objects of the invention will become more apparent from the following detailed description of the preferred embodiment of the invention, which when taken together with the accompanying drawings in which.

Corresponding reference characters indicate corresponding parts throughout the several views of the drawings.

DETAILED DESCRIPTION OF THE PREFERRED EMBODIMENT

Figure 1:
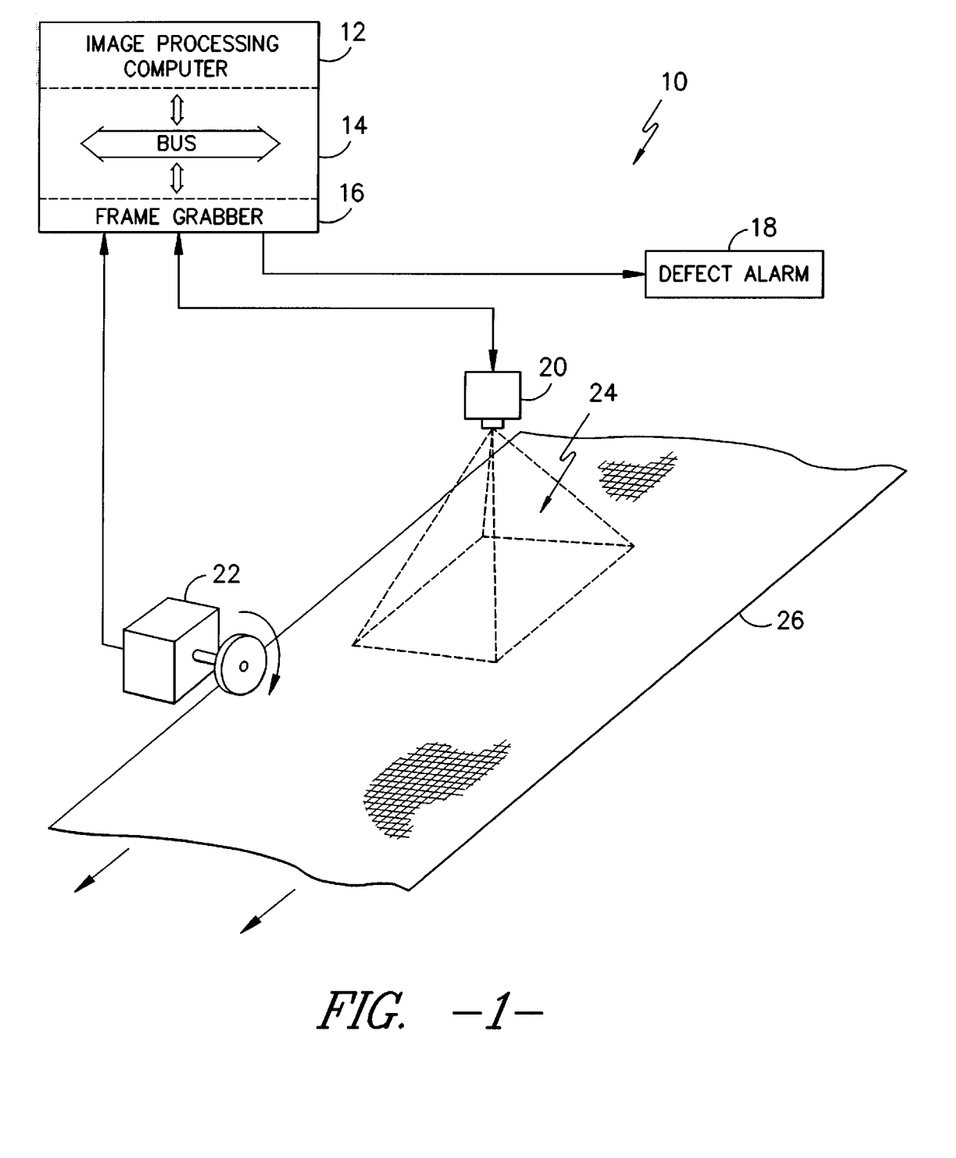
FIG. 1 is a diagrammatic representation, showing the role of various components utilized in and inspecting textile fabric of the present invention such as an image processing computer connected by means of a bus to a frame grabber that is connected to a video camera, defect alarm, and encoder.

This invention is directed to a method and apparatus for inspecting textile fabric. Referring now by the accompanying drawings, and initially to FIG. 1, a textile fabric inspection system is generally indicated by numeral 10. This includes a textile fabric 26 that can be moveable on a conveyor. This textile fabric 26 can be of virtually any type of relatively flat, solid shade, textile fabric including those that are woven, knit, nonwoven, and so forth. Images of the textile fabric 26 are generated by means of a video camera 20. This video camera 20 can be any of a variety of commercially available CCD cameras. A preferred example includes, but not limited to, a monochrome CCD sensor camera such as Model CL-C3-1024 manufactured by Dalsa located at Waterloo, Ontario, Canada. This video camera 20 can be either a line scan or area scan camera that creates a representation of the fabric surface in terms of an array of numbers. Each number corresponds to a specific pixel on the CCD array and ranges from zero (0) for black and $2^n-1$ (for white), where n is the number of bits of digital resolution. In the illustrative video camera, n equals eight (8) and white has a value of two hundred and fifty-five (255). This array of numbers represents the field of view of the video camera 20 and is hereinafter referred to as an image array 24. As shown in FIG. 1, when the video camera 20 is focused on a textile fabric 26, then the image array 24 will represent an array of numbers that represent the relative lightness and darkness attributes between zero (0) and two hundred and fifty-five (255) of the portion of the textile fabric 26 that is visible to the video camera 20. This image array 24 is transmitted to a frame grabber 16 or other frame acquisition device within an image processing computer 12. The image processing computer 12 can be a pipeline processor, a digital signal processor, or a personal computer. Image data is transferred from the frame grabber 16 to the image processing computer 12 via a data bus 14. A preferred example of a pipeline processor would be a MAX VIDEO 200 manufactured by Datacube located in Danvers, Mass. A representative, but nonlimiting example of a frame grabber that would be used with a personal computer would be a Data Raptor—VL that is manufactured by Bitflow located at Woburn, Mass. The use of an image processing computer 20, frame grabber 16, and video camera 20 is disclosed in U.S. Pat. No. 5,394,183 that issued Feb. 28, 1995, which is incorporated by reference as if fully set forth herein.

The image processing computer 12 is also connected to a defect alarm 18. Examples of a defect alarms could include a wide variety of buzzers, lights, and so forth. This would provide a signal to alert the operator when an actual defect is detected in the textile fabric 26. There is an encoder 22 that is able to correlate the position of the textile fabric 26 with the image array 24. The encoder 22 is connected to the frame grabber 16. Illustrative but non-limiting example of an encoder would be RPGB manufactured by Red Lion Controls located at 20 Willow Springs Circle, York, Pa. 17402.

Figure 2:
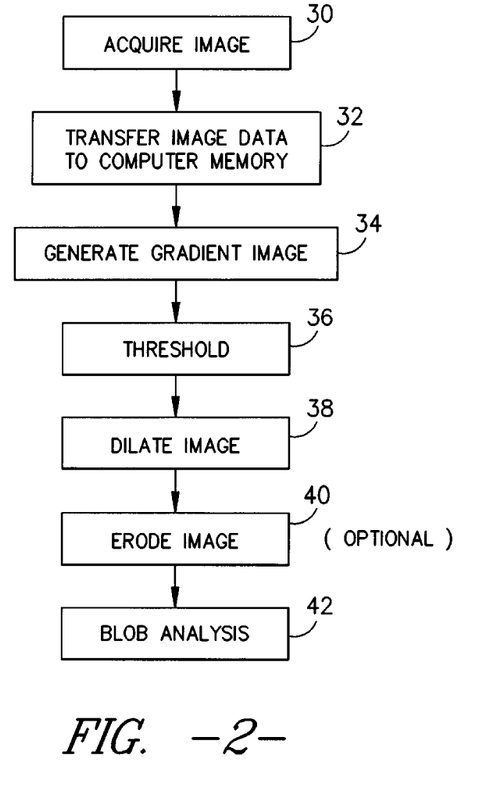
FIG. 2 is a basic flow chart of the processing steps involved with textile fabric inspection system of the present invention.

FIG. 2 is the basic general process steps required to inspect a textile fabric 26. The first step is to acquire an image array 24 of the textile fabric 26 that is in the field of view of the video camera 20 as indicated by numeral 30. This information is transferred to the frame grabber 16 and then transferred to the memory of the image processing computer 12 by means of a bus 14 in step two as indicated by numeral 32 in FIG. 2. As previously stated, the video camera 20, if using a monochrome CCD sensor camera with either line scan or area scan, creates a representation of the surface of the textile fabric 26 in terms of an image array 24 of numbers. Each number corresponds to a specific pixel on the CCD array and ranges from zero (0) for a completely black pixel to $2^n-1$ for completely white pixel, where n is the number of bits of digital resolution. A typical CCD array is 1024×1024 pixels. As previously mention, n equals eight (8) when using the illustrative video camera 20 described above.

The defining attribute of this inspection approach is how the gradient image is generated, which is step three that is depicted by numeral 34 in FIG. 2. Gradient images are useful for detecting transitions in gray levels that represents lines, edges, point defects, and other spatial discontinuities. The gradient image is generated by convolving an image with a structuring element, known as a mask, that is designed to enhance the feature of interest. There are many such structuring elements or masks. Two of these are known as Sobel operators.

Figure 3:
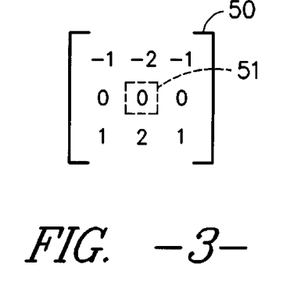
FIG. 3 is a first three by three (3×3) Sobel operator.

As shown in FIG. 3, there is first mask 50 that is used for detecting horizontal edges or lines. This first mask 50 is in the form of a three by three (3×3) operator array that multiplies a specific pixel by zero which is the center number in the array as designated by numeral 51. It then multiplies all surrounding pixels by a −1, −2, −1, 0, 1, 2, 1, and 0 respectively from left to right in a counter-clockwise fashion, as shown in FIG. 3. The summation of all of these multiplied values is the new replacement value for this specific pixel of interest. If there are no spatial discontinuities from top to bottom, then the pixels above the pixel of interest will be multiplied by a negative number that is equivalent to the multipliers below the pixel of interest. Therefore, if the pixel numbers are relatively the same, the summation will be close to zero.

Figure 4:
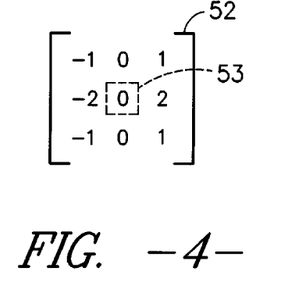
FIG. 4 is a second three by three (3×3) Sobel operator.

As shown in FIG. 4, there is second mask 52 that is used for detecting vertical edges or lines. This second mask 52 is also in the form of a three by three (3×3) operator array that multiplies a specific pixel by zero which is the center number in the array as designated by numeral 53. The negative multipliers are in the form of columns so that the left column and the right column are mirror images. Once again, you multiply all surrounding pixels by a −1, −2, −1, 0, 1, 2, 1, and 0 respectively from left to right in a counter-clockwise fashion, as shown in FIG. 4. The summation of all of these multiplied values is the new replacement value for this specific pixel of interest. If there are no spatial discontinuities from left to right, then the pixels to the left of the pixel of interest will be multiplied by a negative number that is equivalent to the multipliers to the right of the pixel of interest. Therefore, if there are no spatial discontinuities in the vertical direction, the total summation will be close to zero.

Figure 5:
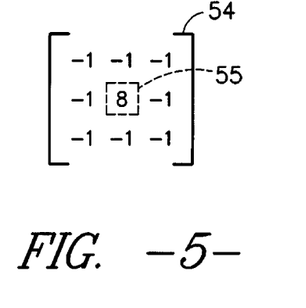
FIG. 5 is a point defect mask that identifies pixels that neighboring pixels having significantly different grey levels.

As shown in FIG. 5, there is third mask 54 that is used for detecting neighboring pixels of a significantly different grey level for detecting point defects. This third mask 54 is also in the form of a three by three (3×3) operator array that multiplies a specific pixel by eight (8) which is the center number in the array surrounded by negative ones as designated by numeral 55. The negative one multipliers surround the eight (8) in the center so that you multiply all surrounding pixels by a −1, −1, −1, −1, −1, −1, −1, and −1 respectively in a counter-clockwise fashion, as shown in FIG. 5. The summation of all of these multiplied values is the new replacement value for this specific pixel of interest. If there are no point defects in the textile fabric 26, the total summation will be close to zero.

There are many defects in the textile fabric 26 that can be detected using the structuring elements or masks found in FIGS. 3, 4, and 5. However, some defects are not detected by using these operators. These hard to detect defects are characterized by very gradual gray level spatial transitions. Examples of some of these include dirt smudges and oil spots in which the oil wicks into the surrounding textile fabric.

Figure 6:
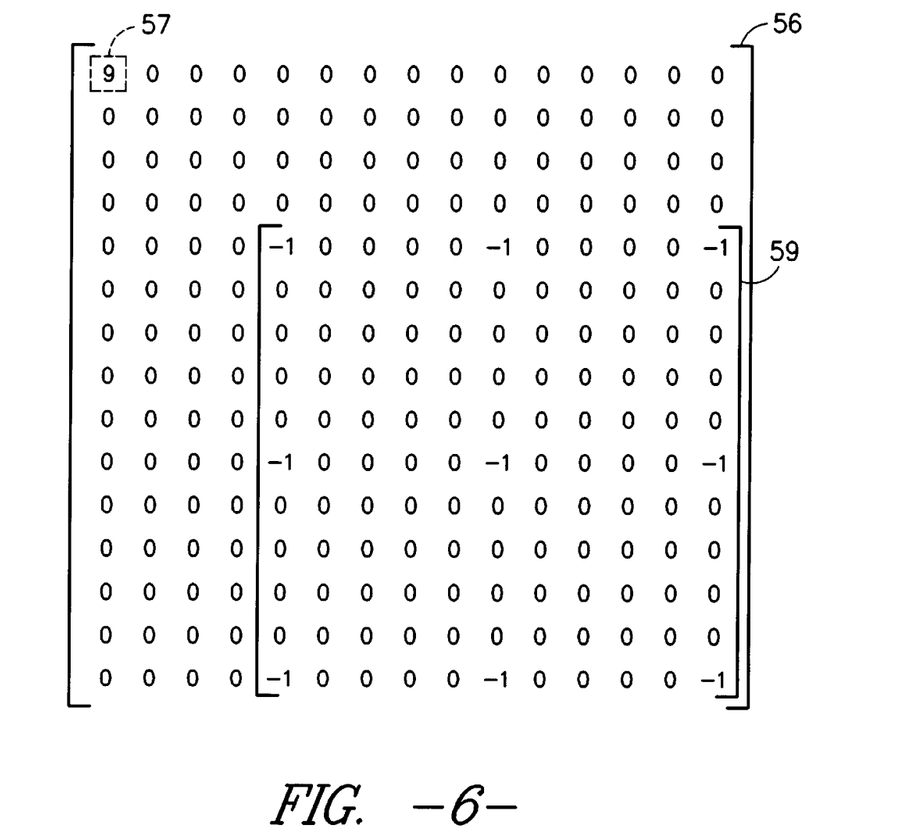
FIG. 6 is a gradient image generator in the form of a trailer mask.

The third step in the inspection process, indicated by numeral 34 in FIG. 2, is to generate a gradient image in which the slow gray level transition defects are identifiable. A new type of structuring element or mask is utilized as indicated by numeral 56, as shown in FIG. 6. The concept is to separate the balancing elements in the mask 56. The positive portion of the mask 56 is represented by the single element having the value of nine (9) as indicated by numeral 57 in FIG. 6. The negating portion of the mask 56 is the sub-array containing negative ones (−1) and zeros (0) as indicated by numeral 59. By separating the balancing portions of the mask 56, very subtle gray level transitions are easily detected.

The positive portion 57 functions exactly like the specific pixel of interest in masks 50, 52, and 54 so that you multiply all surrounding pixels by the mask 56. The summation of all of these multiplied values is the new replacement value for this specific positive element 57.

The size of the mask 56, the negating elements 59 and the location of the positive element 57 need to be chosen by parametric analysis for a particular application. The mask 56 shown in FIG. 6 is specifically designed for a clean wipe textile fabric. One of the disadvantages of the mask 56 is that the mask 56 is not balanced. This means that defects would be translated and distorted in the gradient image with the accurate size of the defect being much more difficult to ascertain.

Figure 7:
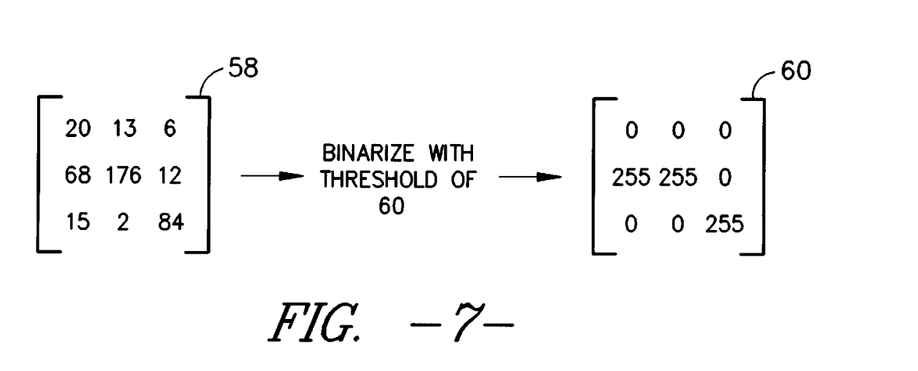
FIG. 7 is a gradient image prior to being thresholded and gradient image after being thresholded with a threshold value of sixty (60) so that all pixels with grey levels above sixty (60) are set to white or two hundred and fifty-five (255) and all pixels equal to or below sixty (60) are set to black or zero(0)

The next step, as shown in FIG. 7, is to threshold the gradient image to separate possible defect pixels from non-defect pixels as shown in the fourth step identified as numeral 36 in FIG. 2. Pixels with gray levels above the threshold are set to white which is a binary number of two hundred and fifty-five (255), with the illustrative video camera 20, while pixels of gray levels below the threshold are set to black with a binary value of zero (0). The preferred binary threshold is that of sixty (60) for clean wipes. This value depends entirely on the textile fabric and the amount of light. AS shown in FIG. 7, a representative three by three (3×3) pixel array 58 is transformed to values of zero (0) and two hundred and fifty-five (255) based on a binary threshold of sixty (60) and is converted into the transform array delineated by numeral 60.

Figure 9:
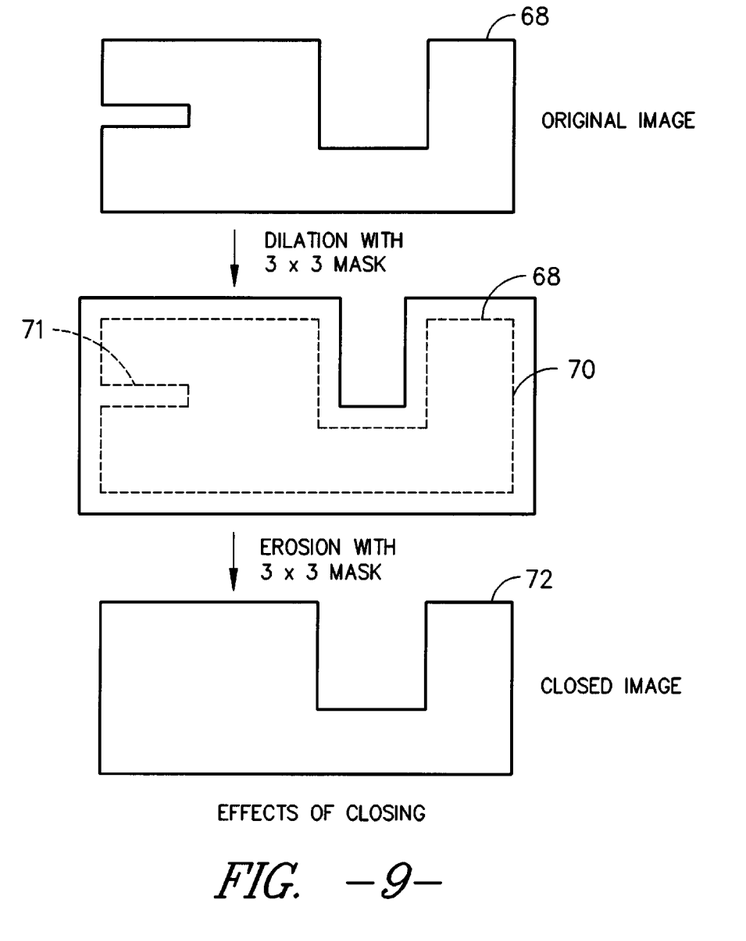
FIG. 9 reveals an original image that is dilated with a three by three (3×3) mask then eroded with a three by three (3×3) mask to form the final closed image.
Figure 10:
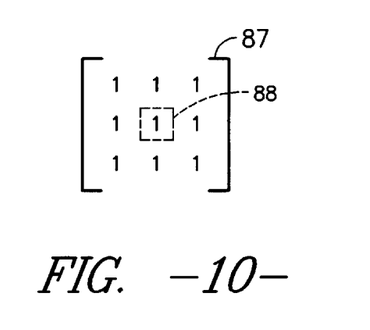
FIG. 10 is a three by three (3×3) array used for dilation and erosion of an image array.

Referring again to FIG. 2, the next process step five, as indicated by numeral 38, is to dilate the image. This operation is necessary to further segregate the defect pixels from the noise pixels. This is done by dilating an original image by a three by three (3×3) array mask 87, as shown in FIG. 10 consisting of all ones (1) with a center pixel of special interest 88. The result of this dilation is shown in FIG. 9, where this step of dilating the image involves passing the center pixel of special interest 88 over each pixel in the image array 68 and multiplying not only this pixel by one (1) but all eight (8) surrounding pixels by one (1) also and determining which pixel of the nine (9) pixels in the three by three (3×3) array, that are being evaluated, has the maximum grey scale value. You would then replace each image pixel within the image array 68 with the maximum grey scale value of either the grey scale value of that specific pixel or the grey scale value of the eight (8) surrounding pixels. This creates a border 70 around the entire image. Therefore, a small indented area 71 is eliminated. This will show the true defect pixels clustered together and will connect these closely spaced defect pixels making them easier to detect since they are now connected objects.

As shown in FIG. 2, the next process step 40 is optional, which is to erode the dilated image 70 with the same three by three (3×3) array or matrix 87, as shown in FIG. 10 consisting of all ones (1) with a center pixel of special interest 88. The result of this erosion is shown in FIG. 9, where this step of eroding the image involves passing the center pixel of special interest 88 over each pixel in the dilated image array 70 and multiplying not only this pixel by one (1) but all eight (8) surrounding pixels by one (1) also and determining which pixel of the nine (9) pixels in the three by three (3×3) array, that are being evaluated, has the minimum grey scale value. You would then replace each image pixel within the dilated image array 70 with the minimum grey scale value of either the grey scale value of that specific pixel or the grey scale value of the eight (8) surrounding pixels. This step as shown in FIG. 9, removes the artificial border of the dilated image 70 while wiping out the indented area 71. This forms the resulting eroded image 72 which is now closed. This returns the objects to their original size while the pixel-to-pixel connection is established during dilation are preserved with this optional step.

Figure 8:
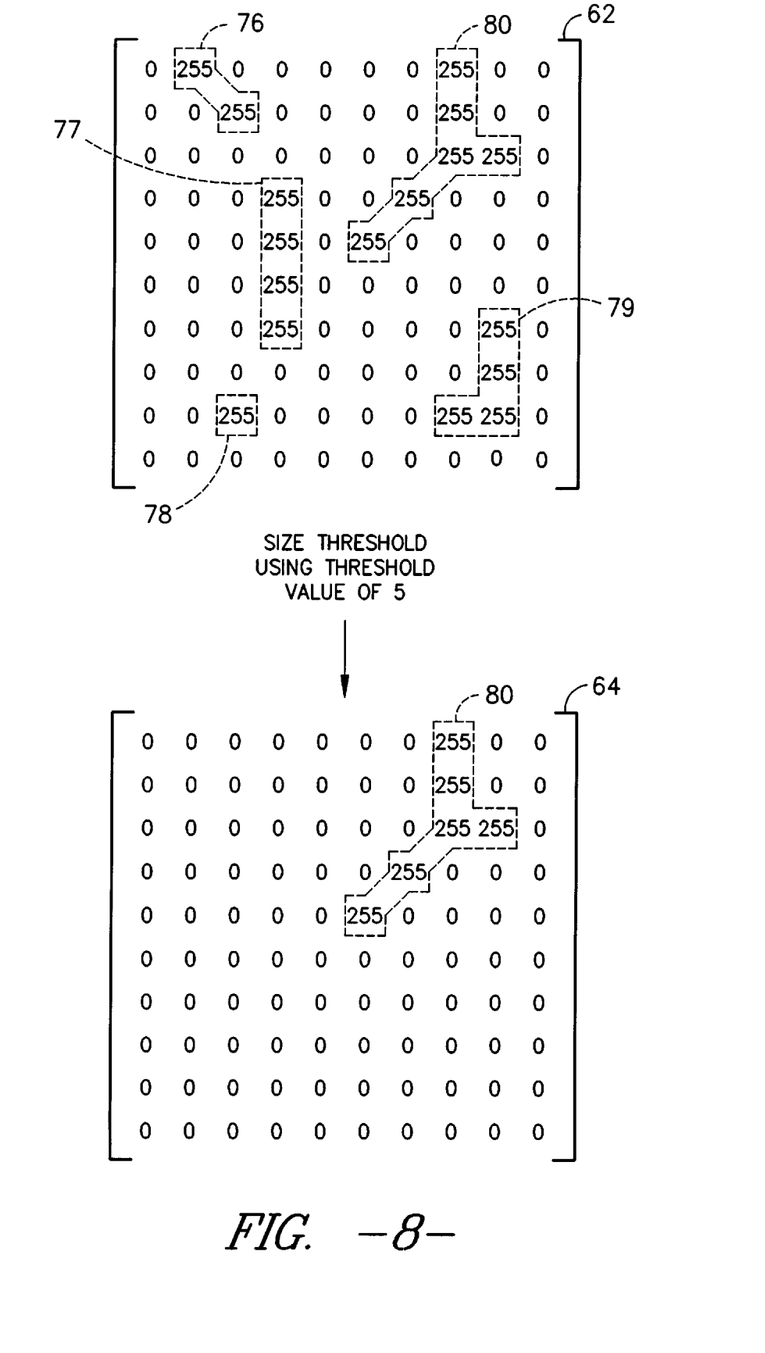
FIG. 8 is a gradient image that has been thresholded in the same manner as FIG. 7, but this image array is then thresholded with respect to size so that all pixels with grey levels of two hundred and fifty-five (255) that are adjacent and in a cluster of pixels of less than five (5) are set to black or zero (0) while all pixels with grey levels of white or two hundred and fifty-five (255) that are adjacent and in a cluster of pixels of five (5) or more retain their grey level value of white or two hundred and fifty-five (255)

The last process step is blob analysis as shown by numeral 42, in FIG. 2. This operation occurs once the morphological operations of dilation and erosion are complete. This step 42 labels connected pixels as objects. A size threshold is defined as those objects whose size exceeds a certain threshold value are classified as defects, while those objects that fall below the threshold value are disregarded. As shown in FIG. 8, which depicts a ten by ten (10×10) array 64 that has been previously thresholded, dilated, and optionally eroded, so that pixels with gray levels above the threshold are set to two hundred and fifty-five (255), while all pixels below the threshold are set to black or zero (0). There are four (4) clusters of adjacent pixels having a value of two hundred and fifty-five (255) that are indicated by numerals 76, 77, 78, 79, and 80. Cluster 76 has only two (2) pixels having a grey scale value of two hundred and fifty-five (255) that are adjacent. Cluster 77 has only four (4) pixels having a grey scale value of two hundred and fifty-five (255) that are adjacent. Cluster 78 is not really a cluster, but a single solitary pixel having a grey scale value of two hundred and fifty-five (255) surrounded by pixels having a grey scale value of zero (0). Cluster 79, like Cluster 77, has only four (4) pixels having a grey scale value of two hundred and fifty-five (255) that are adjacent. Cluster 80 has six (6) pixels having a grey scale value of two hundred and fifty-five (255) that are adjacent. Then using an adjacent size threshold value of five (5), the only cluster of adjacent pixels, having a grey scale value of two hundred and fifty-five (255) and having no zero (0) pixels that separates a group or individual pixel from the rest of the cluster only occurs in Cluster 80 with a value of six (6) adjacent pixels having a grey scale value of two hundred and fifty-five (255). Clusters 76, 77, 78, and 79 all fall below the adjacent size threshold of five (5). The ten by ten (10×10) array represented by numeral 64 shows all of the white pixels set at two hundred and fifty-five (255) above the threshold in Cluster 80. All of the pixels in Clusters 76, 77, 78, and 79 are set to zero (0). Therefore, in this example, there is only one location in which the threshold value of size exceeded the limit of five (5) for a textile fabric—clean room wipe. The preferred size threshold for clean room textile fabrics is five (5). This size the threshold will depend on the type of textile fabric and its application.

It is not intended that the scope of the invention be limited to the specific embodiments illustrated and described. Rather, it is intended that the scope of the invention be defined by the appended claims and their equivalents.

What is claimed is:

1. A system for inspecting textile fabric comprising:

(a) a means for assigning numerical brightness attributes for pixels in the field of view of a video camera;

(b) a memory for storing a set of said numerical brightness attributes for said pixels in said field of view of said video camera;

(c) a means for generating a gradient image from said set of numerical brightness attributes for said pixels in said view of said video camera for identifying gradual gray level spatial transitions;

(d) a means for thresholding said set of numerical brightness attributes for said gradient image;

(e) a means for dilating said numerical brightness attributes that have been thresholded; and (f) a means for blob analysis of said numerical brightness attributes for said pixels that have been dilated and thereby identify defects in said textile fabric.

2. A system for inspecting textile fabric as defined in claim 1, wherein said means for assigning numerical brightness attributes for pixels in the field of view of said video camera includes a frame grabber.

3. A system for inspecting textile fabric as defined in claim 1, wherein said memory for storing a set of said numerical brightness attributes for said pixels in said field of view of said video camera includes a computer.

4. A system for inspecting textile fabric as defined in claim 1, wherein said means for blob analysis of said numerical brightness attributes for said pixels that have been dilated includes a means for labeling connected pixels as objects and only classifying those objects above a size threshold as defects.

5. A system for inspecting textile fabric as defined in claim 1, wherein said textile fabric is a clean room wipe.

6. A system for inspecting textile fabric as defined n claim 1, wherein said means for generating a gradient image from said set of numerical brightness attributes for said pixels in said view of said video camera includes a plurality of masks.

7. A system for inspecting textile fabric as defined in claim 6, wherein said plurality of masks include the following arrays:

$$\begin{vmatrix} -1 & -2 & -1 \\ 0 & 0 & 0 \\ 1 & 2 & 1 \end{vmatrix}$$

$$\begin{vmatrix} -1 & 0 & 1 \\ -2 & 0 & 2 \\ -1 & 0 & 1 \end{vmatrix}$$

$$\begin{vmatrix} -1 & -1 & -1 \\ -1 & 8 & -1 \\ -1 & -1 & -1 \end{vmatrix};$$

8. A system for inspecting textile fabric as defined in claim 1, wherein said means for thresholding said set of numerical brightness attributes for said gradient image includes a means for converting all numeral brightness attributes of said pixels below a threshold value to substantially a lowest value and for converting the numerical brightness attributes of said pixels above said threshold value to substantially a highest numerical brightness value.

9. A system for inspecting textile fabric as defined in claim 8, wherein said means for thresholding said set of numerical brightness attributes for said pixels in said gradient image includes a means for converting said numeral brightness attribute of said pixels that have bee converted to said substantially highest numerical brightness attribute value to said substantially lowest numerical brightness attribute value if said number of pixels that are of said substantially highest numerical brightness value are located in proximity to each other in a cluster does not exceed a size threshold.

10. A system for inspecting textile fabric as defined in claim 1, wherein said means for thresholding said set of numerical brightness attributes for said pixels in said field of view of said video camera includes a means for converting all numeral brightness attributes of said pixels below a threshold value to substantially a value of representing the color black and for converting said set of numerical brightness attributes of said pixels above said threshold value to substantially a value representing the color white.

11. A system for inspecting textile fabric as defined in claim 10, wherein said color white has a numerical brightness attribute of zero (0).

12. A system for inspecting textile fabric as defined in claim 10, wherein said color black has a numerical brightness attribute of two hundred and fifty-five (255).

13. A system for inspecting textile fabric as defined in claim 1, wherein said means for dilating said numerical brightness attributes that have been thresholded includes a mask.

14. A system for inspecting textile fabric as defined in claim 13, wherein said mask includes a three by three (3×3) array.

15. A system for inspecting textile fabric as defined in claim 14, wherein said three by three (3×3) array includes the following:

$$\begin{vmatrix} 1 & 1 & 1 \\ 1 & 1 & 1 \\ 1 & 1 & 1 \end{vmatrix}.$$

16. A system for inspecting textile fabric as defined in claim 1, wherein said means for generating a gradient image from said set of numerical brightness attributes for said pixels in said view of said video camera for identifying gradual gray level spatial transitions includes a mask.

17. A system for inspecting textile fabric as defined in claim 16, wherein said mask includes a Sobel operator.

18. A system for inspecting textile fabric as defined in claim 16, wherein said mask includes a three by three (3×3) operator array.

19. A system for inspecting textile fabric as defined in claim 16, where in said mask includes the following array:

$$\begin{vmatrix} -1 & -2 & -1 \\ 0 & 0 & 0 \\ 1 & 2 & 1 \end{vmatrix}.$$

20. A system for inspecting textile fabric as defined in claim 16, wherein said mask includes the following array:

$$\begin{vmatrix} -1 & 0 & 1 \\ -2 & 0 & 2 \\ -1 & 0 & 1 \end{vmatrix}.$$

21. A system for inspecting textile fabric as defined in claim 16, wherein said mask includes the following array:

$$\begin{vmatrix} -1 & -1 & -1 \\ -1 & 8 & -1 \\ -1 & -1 & -1 \end{vmatrix}.$$

22. A system for inspecting textile fabric as defined in claim 16, wherein said plurality of masks include the following arrays:

$$\begin{vmatrix} -1 & -2 & -1 \\ 0 & 0 & 0 \\ 1 & 2 & 1 \end{vmatrix}$$

$$\begin{vmatrix} -1 & 0 & 1 \\ -2 & 0 & 2 \\ -1 & 0 & 1 \end{vmatrix}$$

$$\begin{vmatrix} -1 & -1 & -1 \\ -1 & 8 & -1 \\ -1 & -1 & -1 \end{vmatrix}$$

$$\begin{vmatrix} 9 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \end{vmatrix}$$

23. A system for inspecting textile fabric as defined in claim 16, wherein said mask includes a pivot element, a negating portion that trails said pivot element and a positive portion that is offset from said negating portion of said mask.

24. A system for inspecting textile fabric as defined in claim 23, wherein said mask includes the following array:

$$\begin{vmatrix} 9 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \end{vmatrix}.$$

25. A system for inspecting textile fabric comprising:
(a) a means for assigning numerical brightness attributes for pixels in the field of view of a video camera;
(b) a memory for storing a set of said numerical brightness attributes for said pixels in said field of view of said video camera;
(c) a means for generating a gradient image from said set of numerical brightness attributes for said pixels in said view of said video camera for identifying gradual gray level spatial transitions;
(d) a means for thresholding said set of numerical brightness attributes for said gradient image;
(e) a means for dilating said numerical brightness attributes that have been thresholded;
(f) a means for eroding said numerical brightness attributes that have been dilated; and
(g) a means for blob analysis of said numerical brightness attributes for said pixels that have been dilated and thereby identify defects in said textile fabric.

26. A system for inspecting textile fabric as defined in claim 25, wherein said means for eroding said numerical brightness attributes that have been dilated includes a mask.

27. A system for inspecting textile fabric as defined in claim 26, wherein said mask includes a three by three (3×3) array.

28. A system for inspecting textile fabric as defined in claim 27, wherein said three by three (3×3) array includes the following:

$$\begin{vmatrix} 1 & 1 & 1 \\ 1 & 1 & 1 \\ 1 & 1 & 1 \end{vmatrix}.$$

29. A process for inspecting textile fabric comprising the steps of:
(a) assigning numerical brightness attributes for pixels in the field of view of a video camera;
(b) storing a set of said numerical brightness attributes for said pixels in said field of view of said video camera;
(c) generating a gradient image from said set of numerical brightness attributes for said pixels in said view of said video camera for identifying gradual grey level spatial transitions;
(d) thresholding said set of numerical brightness attributes for said gradient image;
(e) dilating said numerical brightness attributes that have been thresholded; and
(f) analyzing blobs of said numerical brightness attributes for said pixels that have been dilated and thereby identify defects in said textile fabric.

30. A process for inspecting textile fabric comprising the steps of:
(a) assigning numerical brightness attributes for pixels in the field of view of a video camera with a frame grabber;
(b) storing as set of said numerical brightness attributes for said pixels in said field of view of said video camera;
(c) generating a gradient image from said set of numerical brightness attributes for said pixels in said view of said video camera for identifying gradual gray level spatial transitions;
(d) thresholding said set of numerical brightness attributes for said gradient image;
(e) dilating said numerical brightness attributes that have been thresholded; and
(f) analyzing blobs of said numerical brightness attributes for said pixels that have been dilated and thereby identify defects in said textile fabric.

31. A process for inspecting textile fabric comprising the steps of:
(a) assigning numerical brightness attributes for pixels in the field of view of a video camera;
(b) storing a set of said numerical brightness attributes for said pixels in said field of view of said video camera with a computer;
(c) generating a gradient image from said set of numerical brightness attributes for said pixels in said view of said video camera for identifying gradual gray level spatial transitions;
(d) thresholding said set of numerical brightness attributes for said gradient image;
(e) dilating said numerical brightness attributes that have been thresholded; and
(f) analyzing blobs of said numerical brightness attributes for said pixels that have been dilated and thereby identify defects in said textile fabric.

32. A process for inspecting textile fabric comprising the steps of:
(a) assigning numerical brightness attributes for pixels in the field of view of a video camera;
(b) storing a set of said numerical brightness attributes for said pixels in said field of view of said video camera;
(c) generating a gradient image from said set of numerical brightness attributes for said pixels in said view of said video camera for identifying gradual gray level spatial transitions with a mask;
(d) thresholding said set of numerical brightness attributes for said gradient image;
(e) dilating said numerical brightness attributes that have been thresholded; and
(f) analyzing blobs of said numerical brightness attributes for said pixels that have been dilated and thereby identify defects in said textile fabric.

33. A process for inspecting textile fabric comprising the steps of:
(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera for identifying gradual gray level spatial transitions with plurality of three by three (3×3) operator arrays;

(d) thresholding said set of numerical brightness attributes for said gradient image;

(e) dilating said numerical brightness attributes that have been thresholded; and (f) analyzing blobs of said numerical brightness attributes for said pixels that have been dilated and thereby identify defects in said textile fabric.

34. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera for identifying gradual gray level spatial transitions with the following the three by three (3×3) operator arrays:

$$\begin{vmatrix} -1 & -2 & -1 \\ 0 & 0 & 0 \\ 1 & 2 & 1 \end{vmatrix}$$

$$\begin{vmatrix} -1 & 0 & 1 \\ -2 & 0 & 2 \\ -1 & 0 & 1 \end{vmatrix}$$

$$\begin{vmatrix} -1 & -1 & -1 \\ -1 & 8 & -1 \\ -1 & -1 & -1 \end{vmatrix};$$

(d) thresholding said set of numerical brightness attributes for said gradient image;

(e) dilating said numerical brightness attributes that have been thresholded; and (f) analyzing blobs of said numerical brightness attributes for said pixels that have been dilated and thereby identify defects in said textile fabric.

35. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera for identifying gradual gray level spatial transitions with a mask wherein said mask includes a pivot element, a negating portion that trails said pivot element and a positive portion that is offset from said negating portion of said mask;

(d) thresholding said set of numerical brightness attributes for said gradient image;

(e) dilating said numerical brightness attributes that have been thresholded; and (f) analyzing blobs of said numerical brightness attributes for said pixels that have been dilated and thereby identify defects in said textile fabric.

36. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera for identifying gradual gray level spatial transitions with the following three by three (3×3) operator arrays:

$$\begin{vmatrix} -1 & -2 & -1 \\ 0 & 0 & 0 \\ 1 & 2 & 1 \end{vmatrix}$$

$$\begin{vmatrix} -1 & 0 & 1 \\ -2 & 0 & 2 \\ -1 & 0 & 1 \end{vmatrix}$$

$$\begin{vmatrix} -1 & -1 & -1 \\ -1 & 8 & -1 \\ -1 & -1 & -1 \end{vmatrix}$$

$$\begin{vmatrix} 9 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 & 0 \\ 0 & 0 & 0 & 0 & -1 & 0 & 0 & 0 & 0 & -1 & 0 & 0 & 0 & 0 & -1 \end{vmatrix};$$

(d) thresholding said set of numerical brightness attributes for said gradient image;

(e) dilating said numerical brightness attributes that have been thresholded; and (f) analyzing blobs of said numerical brightness attributes for said pixels that have been dilated and thereby identify defects in said textile fabric.

37. A process for inspecting textile fabric comprising the steps of:

(a) assigning numerical brightness attributes for pixels in the field of view of video camera;

(b) storing a set of said numerical brightness attributes for said pixels in said field of view of said video camera:

(c) generating a gradient image from said set of numerical brightness attributes for said pixels in said view of said video camera;

(d) thresholding said set of numerical brightness attributes for said gradient image by converting all numeral brightness attributes of said pixels below a threshold value to substantially a lowest value and for converting the numerical brightness attributes of said pixels above said threshold value to substantially a highest numerical brightness value;

(e) dilating said numerical brightness attributes that have been thresholded; and (f) analyzing blobs of said numerical brightness attributes for said pixels that have been dilated and thereby identify defects in said textile fabric.

38. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera;

(d) thresholding said set of numerical brightness attributes for said gradient image by converting all numeral brightness attributes of said pixels below a threshold value to substantially a value of representing the color black and for converting the numerical brightness attributes of said pixels above said threshold value to substantially a value representing the color white;

(e) dilating said numerical brightness attributes that have been thresholded; and (f) analyzing blobs of said numerical brightness attributes for said pixels that have been dilated and thereby identify defects in said textile fabric.

39. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera;

(d) thresholding said set of numerical brightness attributes for said gradient image;

(e) dilating said numerical brightness attributes that have been thresholded with a mask; and (f) analyzing blobs of said numerical brightness attributes for said pixels that have been dilated and thereby identify defects in said textile fabric.

40. A process for inspecting textile fabric comprising the steps; of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera;

(d) thresholding said set of numerical brightness attributes for said gradient image;

(e) dilating said numerical brightness attributes that have been thresholded with a mask wherein said mask is a three by three (3×3) array; and (f) analyzing blobs of said numerical brightness attributes for said pixels that have been dilated and thereby identify defects in said textile fabric.

41. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera;

(d) thresholding said set of numerical brightness attributes for said gradient image;

(e) dilating said numerical brightness attributes that have been thresholded with a mask wherein said mask is the following three by three (3×3) array:

$$\begin{vmatrix} 1 & 1 & 1 \\ 1 & 1 & 1 \\ 1 & 1 & 1 \end{vmatrix}.$$

and (f) analyzing blobs of said numerical brightness attributes for said pixels that have been dilated and thereby identify defects in said textile fabric.

42. A process for inspecting textile fabric comprising the steps of:

(a) assigning numerical brightness attributes for pixels in. the field of view of a video camera;

(b) storing a set of said numerical brightness attributes for said pixels in said field of view of said video camera;

(c) generating a gradient image from said set of numerical brightness attributes for said pixels in said view of said video camera;

(d) thresholding said set of numerical brightness attributes for said gradient image;

(e) dilating said numerical brightness attributes that have been thresholded; and (f) analyzing blobs of said numerical brightness attributes for said pixels that have been dilated by labeling connected pixels as objects and only classifying those objects above a size threshold as defects and thereby identifying defects in said textile fabric.

43. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera;

(d) thresholding said set of numerical brightness attributes for said gradient image;

(e) dilating said numerical brightness attributes that have been thresholded;

(f) eroding said numerical brightness attributes that have been dilated; and (g) analyzing blobs of said numerical brightness attributes for said pixels that have been dilated and thereby identify defect in said textile fabric.

44. A process for inspecting textile fabric comprising the steps of:

(a) assigning numerical brightness attributes for pixels in the field of view of a video camera;

(b) storing a set of said numerical brightness attributes for said pixels in said field of view of said video camera;

(c) generating a gradient image from said set of numerical brightness attributes for said pixels in said view of said video camera;

(d) thresholding said set of numerical brightness attributes for said gradient image;
(e) dilating said numerical brightness attributes that have been thresholded;
(f) eroding said numerical brightness attributes that have been dilated with a mask; and
(g) analyzing blobs of said numerical brightness attributes for said pixels that have been dilated and thereby identify defects in said textile fabric.

45. A process for inspecting textile fabric comprising the steps of:
(a) assigning numerical brightness attributes for pixels in the field of view of a video camera;
(b) storing a set of said numerical brightness attributes for said pixels in said field of view of said video camera;
(c) generating a gradient image from said set of numerical brightness attributes for said pixels in said view of said video camera;
(d) thresholding said set of numerical brightness attributes for said gradient image;
(e) dilating said numerical brightness attributes that have been thresholded;
(f) eroding said numerical brightness attributes that have been dilated with a three by three (3×3) array; and
(g) analyzing blobs of said numerical brightness attributes for said pixels that have been dilated and thereby identify defects in said textile fabric.

46. A process for inspecting textile fabric comprising the steps: of:
(a) assigning numerical brightness attributes for pixels in the field of view of a video camera;
(b) storing a set of said numerical brightness attributes for said pixels in said field of view of said video camera;
(c) generating a gradient image from said set of numerical brightness attributes for said pixels in said view of said video camera;
(d) thresholding said stet of numerical brightness attributes for said gradient image;
(e) dilating said numerical brightness attributes that have been thresholded;
(f) eroding said numerical brightness attributes that have been dilated with the following three by three (3×3) array:

$$\begin{vmatrix} 1 & 1 & 1 \\ 1 & 1 & 1 \\ 1 & 1 & 1 \end{vmatrix}.$$

and
(g) analyzing blobs of said numerical brightness attributes for said pixels that have been dilated and thereby identify defects in said textile fabric.

47. A process for inspecting textile fabric comprising the steps of:
(a) assigning numerical brightness attributes for pixels in the field of view of a video camera;
(b) storing a set of said numerical brightness attributes for said pixels in said field of view of said video camera;
(c) generating a gradient image from said set of numerical brightness attributes for said pixels in said view of said video camera;
(d) thresholding said set of numerical brightness attributes for said gradient image by converting said numeral brightness attributes of said pixels that have been converted to said substantially highest numerical. brightness attribute value to said substantially lowest numerical brightness attribute value if said number of pixels that are of said substantially highest numerical brightness value are located in proximity to each other in a cluster does not exceed a size threshold;
(e) dilating said numerical brightness attributes for said pixels that have been thresholded; and
(f) analyzing blobs of said numerical brightness attributes for said pixels that have been dilated and thereby identify defects in said textile fabric.

48. A process for inspecting clean room wipes comprising the step of:
(a) assigning numerical brightness attributes for pixels in the field of view of a video camera:
(b) storing a set of said numerical brightness attributes for said pixels in said field of view of said video camera;
(c) generating a gradient image from said set of numerical brightness attributes for said pixels in said view of said video camera;
(d) thresholding said set of numerical brightness attributes for said gradient image;
(e) dilating said numerical brightness attributes that have been thresholded; and
(f) analyzing blobs of said numerical brightness attributes for said pixels that have been dilated and thereby identify defects in said clean room wipes.

49. A process for inspecting textile fabric comprising the steps of:
(a) assigning numerical brightness attributes for pixels in the field of view of a video camera;
(b) storing a set of said numerical brightness attributes for said pixels in said field of view of said video camera;
(c) generating a gradient image from said set of numerical brightness attributes for said pixels in said view of said video camera;
(d) thresholding said set of numerical brightness attributes for said gradient image;
(e) dilating said numerical brightness attributes that have been thresholded; and
(f) analyzing blobs of said numerical brightness attributes for said pixels that have been dilated by converting said numeral brightness attributes of said pixels that have been converted to said substantially highest numerical brightness attribute value to said substantially lowest numerical brightness attribute value if said number of pixels that are of said substantially highest numerical brightness value are located in proximity to each other in a cluster does not exceed a size threshold and thereby identify defects in said textile fabric.

* * * * *